(12) United States Patent
Griego et al.

(10) Patent No.: US 7,780,611 B2
(45) Date of Patent: Aug. 24, 2010

(54) MEDICAL INSTRUMENT WITH CONTROLLED TORQUE TRANSMISSION

(75) Inventors: John A. Griego, Blackstone, MA (US); Patrice A. Weststrate, Norwood, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 330 days.

(21) Appl. No.: 10/428,240

(22) Filed: May 1, 2003

(65) Prior Publication Data

US 2004/0220499 A1 Nov. 4, 2004

(51) Int. Cl.
A61M 25/00 (2006.01)
A61B 6/00 (2006.01)

(52) U.S. Cl. .................. 600/585; 600/433; 600/434; 600/435

(58) Field of Classification Search ......... 600/433–435, 600/585

See application file for complete search history.

(56) References Cited

U.S. PATENT DOCUMENTS

| | | | |
|---|---|---|---|
| 3,472,230 A | 10/1969 | Fogarty | |
| 3,592,186 A | 7/1971 | Oster | |
| 3,683,904 A | 8/1972 | Forster | |
| 3,889,657 A | 6/1975 | Baumgarten | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,447,227 A | 5/1984 | Kotsanis | |
| 4,580,568 A | 4/1986 | Gianturco | |
| 4,590,938 A | 5/1986 | Segura et al. | |
| 4,619,246 A | 10/1986 | Molgaard-Nielsen et al. | |
| 4,631,052 A | 12/1986 | Kensey | |

(Continued)

FOREIGN PATENT DOCUMENTS

DE 28 21 048 7/1980

(Continued)

OTHER PUBLICATIONS

"annealed." Dictionary.com Unabridged. Random House, Inc. Nov. 16, 2009. <Dictionary.com http://dictionary.reference.com/browse/annealed>.*

(Continued)

Primary Examiner—Max Hindenburg
Assistant Examiner—Jeffrey G Hoekstra
(74) Attorney, Agent, or Firm—Crompton, Seager & Tufte LLC

(57) ABSTRACT

A medical instrument such as a guidewire that is designed to have controlled torque transmission along its length. Specially treated areas are placed in selected and equal areas along the entire length of the elongated shaft of the medical instrument, and are separated from one another by untreated areas. This process ensures that any torque is transmitted distally, in a smooth manner, regardless of the guidewire position, thus resulting in a substantial reduction in whipping. In one embodiment, a stainless steel guidewire is utilized, and is subjected to annealing heat treatment in selected areas. This annealing process creates a mandrel that has repeated temper properties along its length. Torque applied at one end of this mandrel is transmitted to the opposite end in an even and controlled manner, even when the mandrel is formed into a loop.

13 Claims, 5 Drawing Sheets

U.S. PATENT DOCUMENTS

| | | | |
|---|---|---|---|
| 4,643,184 A | 2/1987 | Mobin-Uddin | |
| 4,650,466 A | 3/1987 | Luther | |
| 4,654,092 A | 3/1987 | Melton | |
| 4,662,885 A | 5/1987 | DiPisa, Jr. | |
| 4,705,517 A | 11/1987 | DiPisa, Jr. | |
| 4,706,671 A | 11/1987 | Weinrib | |
| 4,723,549 A | 2/1988 | Wholey et al. | |
| 4,728,319 A | 3/1988 | Masch | |
| 4,733,665 A | 3/1988 | Palmaz | |
| 4,764,324 A | 8/1988 | Burnham | |
| 4,790,812 A | 12/1988 | Hawkins, Jr. et al. | |
| 4,790,813 A | 12/1988 | Kensey | |
| 4,790,831 A | 12/1988 | Skribiski | |
| 4,794,928 A | 1/1989 | Kletschka | |
| 4,794,931 A | 1/1989 | Yock | |
| 4,800,882 A | 1/1989 | Gianturco | |
| 4,807,626 A | 2/1989 | McGirr | |
| 4,842,579 A | 6/1989 | Shiber | |
| 4,857,045 A | 8/1989 | Rydell | |
| 4,857,046 A | 8/1989 | Stevens et al. | |
| 4,867,157 A | 9/1989 | McGurk-Burleson et al. | |
| 4,873,978 A | 10/1989 | Ginsburg | |
| 4,898,575 A | 2/1990 | Fischell et al. | |
| 4,907,336 A | 3/1990 | Gianturco | |
| 4,921,478 A | 5/1990 | Solano et al. | |
| 4,921,484 A | 5/1990 | Hillstead | |
| 4,925,445 A | 5/1990 | Sakamoto et al. | |
| 4,926,858 A | 5/1990 | Giffort, III et al. | |
| 4,950,277 A | 8/1990 | Farr | |
| 4,955,895 A | 9/1990 | Sugiyama et al. | |
| 4,957,482 A | 9/1990 | Shiber | |
| 4,969,891 A | 11/1990 | Gewertz | |
| 4,979,951 A | 12/1990 | Simpson | |
| 4,986,807 A | 1/1991 | Farr | |
| 4,998,539 A | 3/1991 | Delsanti | |
| 5,002,560 A | 3/1991 | Machold et al. | |
| RE33,569 E | 4/1991 | Gifford, III et al. | |
| 5,007,896 A | 4/1991 | Shiber | |
| 5,007,917 A | 4/1991 | Evans | |
| 5,011,488 A | 4/1991 | Ginsburg | |
| 5,019,088 A | 5/1991 | Farr | |
| 5,041,126 A | 8/1991 | Gianturco | |
| 5,053,008 A | 10/1991 | Bajaj | |
| 5,053,044 A | 10/1991 | Mueller et al. | |
| 5,069,226 A | 12/1991 | Yamauchi et al. | |
| 5,071,407 A | 12/1991 | Termin et al. | |
| 5,071,425 A | 12/1991 | Gifford, III et al. | |
| 5,085,662 A | 2/1992 | Willard | |
| 5,087,265 A | 2/1992 | Summers | |
| 5,095,915 A | 3/1992 | Engelson | |
| 5,100,423 A | 3/1992 | Fearnot | |
| 5,100,424 A | 3/1992 | Jang et al. | |
| 5,100,425 A | 3/1992 | Fischell et al. | |
| 5,102,415 A | 4/1992 | Guenther et al. | |
| 5,104,399 A | 4/1992 | Lazarus | |
| 5,108,419 A | 4/1992 | Reger et al. | |
| 5,133,733 A | 7/1992 | Rasmussen et al. | |
| 5,135,531 A | 8/1992 | Shiber | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,171,233 A | 12/1992 | Amplatz et al. | |
| 5,171,383 A | 12/1992 | Sagaye et al. | |
| 5,190,546 A | 3/1993 | Jervis | |
| 5,195,955 A | 3/1993 | Don Michael | |
| 5,224,953 A | 7/1993 | Morgentaler | |
| 5,228,453 A | 7/1993 | Sepetka | |
| 5,238,004 A | 8/1993 | Sahatjian et al. | |
| 5,269,752 A * | 12/1993 | Bennett | 604/28 |
| 5,275,173 A | 1/1994 | Samson et al. | |
| 5,299,580 A | 4/1994 | Atkinson et al. | |
| 5,306,286 A | 4/1994 | Stack et al. | |
| 5,314,444 A | 5/1994 | Gianturco | |
| 5,314,472 A | 5/1994 | Fontaine | |
| 5,318,576 A | 6/1994 | Plassche, Jr. et al. | |
| 5,329,942 A | 7/1994 | Gunther et al. | |
| 5,330,484 A | 7/1994 | Gunther | |
| 5,330,500 A | 7/1994 | Song | |
| 5,333,620 A | 8/1994 | Moutafis et al. | |
| 5,341,818 A | 8/1994 | Abrams et al. | |
| 5,350,398 A | 9/1994 | Pavcnik et al. | |
| 5,354,310 A | 10/1994 | Garnic et al. | |
| 5,356,423 A | 10/1994 | Tihon et al. | |
| 5,366,464 A | 11/1994 | Belknap | |
| 5,366,473 A | 11/1994 | Winston et al. | |
| 5,370,657 A | 12/1994 | Irie | |
| 5,370,683 A | 12/1994 | Fontaine | |
| 5,376,100 A | 12/1994 | Lefebvre | |
| 5,379,779 A | 1/1995 | Rowland et al. | |
| 5,383,887 A | 1/1995 | Nadal | |
| 5,383,892 A | 1/1995 | Cardon et al. | |
| 5,383,926 A | 1/1995 | Lock et al. | |
| 5,385,152 A | 1/1995 | Abele et al. | |
| 5,387,235 A | 2/1995 | Chuter | |
| 5,395,349 A | 3/1995 | Quiachon et al. | |
| 5,397,345 A | 3/1995 | Lazerus | |
| 5,405,377 A | 4/1995 | Cragg | |
| 5,409,454 A | 4/1995 | Fischell et al. | |
| 5,415,630 A | 5/1995 | Gory et al. | |
| 5,419,774 A | 5/1995 | Willard et al. | |
| 5,421,832 A | 6/1995 | Lefebvre | |
| 5,423,742 A | 6/1995 | Theron | |
| 5,423,885 A | 6/1995 | Williams | |
| 5,425,765 A | 6/1995 | Tiefenbrun et al. | |
| 5,443,498 A | 8/1995 | Fontaine | |
| 5,449,372 A | 9/1995 | Schmaltz et al. | |
| 5,456,667 A | 10/1995 | Ham et al. | |
| 5,462,529 A | 10/1995 | Simpson et al. | |
| 5,476,104 A | 12/1995 | Sheahon | |
| 5,484,418 A | 1/1996 | Quiachon et al. | |
| 5,497,786 A * | 3/1996 | Urick | 600/585 |
| 5,507,767 A | 4/1996 | Maeda et al. | |
| 5,512,044 A | 4/1996 | Duer | |
| 5,527,354 A | 6/1996 | Fontaine et al. | |
| 5,536,242 A | 7/1996 | Willard et al. | |
| 5,540,707 A | 7/1996 | Ressemann et al. | |
| 5,549,626 A | 8/1996 | Miller et al. | |
| 5,562,724 A | 10/1996 | Vowerk et al. | |
| 5,569,274 A | 10/1996 | Rapacki et al. | |
| 5,569,275 A | 10/1996 | Kotula et al. | |
| 5,570,701 A * | 11/1996 | Ellis et al. | 600/585 |
| 5,634,897 A | 6/1997 | Dance et al. | |
| 5,637,089 A | 6/1997 | Abrams et al. | |
| 5,658,296 A | 8/1997 | Bates et al. | |
| 5,662,671 A | 9/1997 | Barbut et al. | |
| 5,669,933 A | 9/1997 | Simon et al. | |
| 5,695,519 A | 12/1997 | Summers et al. | |
| 5,709,704 A | 1/1998 | Nott et al. | |
| 5,720,764 A | 2/1998 | Naderlinger | |
| 5,728,066 A | 3/1998 | Daneshvar | |
| 5,746,701 A | 5/1998 | Noone | |
| 5,746,758 A | 5/1998 | Nordgren et al. | |
| 5,749,848 A | 5/1998 | Jang et al. | |
| 5,769,816 A | 6/1998 | Barbut et al. | |
| 5,772,609 A | 6/1998 | Nguyen et al. | |
| 5,779,716 A | 7/1998 | Cano et al. | |
| 5,792,157 A | 8/1998 | Mische et al. | |
| 5,792,300 A | 8/1998 | Inderbitzen et al. | |
| 5,795,322 A | 8/1998 | Boudewijn | |
| 5,797,952 A | 8/1998 | Klein | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |

| Patent No. | Date | Inventor(s) |
|---|---|---|
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,494 A | 9/1999 | Wang et al. |
| 5,951,585 A | 9/1999 | Cathcart et al. |
| 5,954,745 A | 9/1999 | Gertler et al. |
| 5,976,172 A | 11/1999 | Homsma et al. |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,019,736 A * | 2/2000 | Avellanet et al. ............ 600/585 |
| 6,027,520 A | 2/2000 | Tsugita et al. |
| RE36,628 E | 3/2000 | Sagae et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,099,485 A | 8/2000 | Patterson |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,571 B1 | 1/2001 | Solar et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,280,539 B1 | 8/2001 | Abrams et al. |
| 6,287,321 B1 | 9/2001 | Jang |
| 6,290,710 B1 | 9/2001 | Cryer et al. |
| 6,306,105 B1 | 10/2001 | Rooney et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,383,204 B1 * | 5/2002 | Ferrera et al. ............ 606/191 |
| 6,390,993 B1 | 5/2002 | Cornish et al. |
| 6,406,442 B1 | 6/2002 | McFann et al. |
| 6,423,052 B1 | 7/2002 | Escano |
| 6,494,894 B2 | 12/2002 | Mirarchi |
| 6,533,751 B2 | 3/2003 | Cragg et al. |
| 6,544,197 B2 | 4/2003 | DeMello |
| 6,582,536 B2 | 6/2003 | Shimada |
| 6,666,829 B2 | 12/2003 | Cornish et al. |
| 6,682,493 B2 | 1/2004 | Mirigian |
| 7,097,624 B2 * | 8/2006 | Campion et al. ............ 600/585 |
| 2001/0037125 A1 | 11/2001 | Mirarchi |
| 2002/0013540 A1 * | 1/2002 | Jacobsen et al. ............ 600/585 |

FOREIGN PATENT DOCUMENTS

| | | |
|---|---|---|
| DE | 34 17 738 | 11/1985 |
| DE | 40 30 998 A1 | 10/1990 |
| DE | 198 23 414 A | 6/1999 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 266 670 A1 | 12/2002 |
| FR | 2 580 504 | 10/1986 |
| FR | 2 643 250 A1 | 8/1990 |
| FR | 2 666 980 | 3/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |

| | | |
|---|---|---|
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 02/45770 A2 | 6/2002 |

OTHER PUBLICATIONS

"tempered." Dictionary.com Unabridged. Random House, Inc. Nov. 16, 2009. <Dictionary.com http://dictionary.reference.com/browse/tempered>.*

"Atherosclerotic Disease of the Aortic Arch as a Risk Factor of Recurrent Ischemic Stroke," *The New England Journal of Medicine*, pp. 1216-1221 (May 1996).

"Endovascular Grafts, Stents Drive Interventional Radiology Growth," *Cardiovascular Device Update*, 2(3):1-12 (Mar. 1996).

"Protruding Atheromas in the Thoracic Aortic and Systemic Embolization," pp. 423-427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601-604 (Sep. 1983).

Cragg, Andrew et al., "Nonsurgical Placement of Arterial Endoprosthesis: A New Technique Using Nitinol Wire," AJR, pp. 261-263 (Apr. 1983).

Diethrich et al., "Percutaneous Techniques for Endoluminal Carotid Interventions," *J. Endovasc. Surg.*, 3:182-202 (1996).

Fadali, A. Moneim, "A filtering device for the prevention of particulate embolization during the course of cardiac surgery," Surgery, 64(3):634-639 (Sep. 1968).

Haissaguerre et al., "Spontaneous Initiation of Atrial Fibrillation by Ectopic Beats Originating in the Pulmonary Veins," The New England Journal of Medicine, 339(10):659-666 (Sep. 1988).

Jordan, Jr. et al., "Microemboli Detected by Transcranial Doppler Monitoring . . . ," *Cardiovascular Surgery*, 7(1)33-38 (Jan. 1999).

Lesh, "Can Catheter Ablation Cure Atrial Fibrillation?" *ACC Current Journal Review*, pp. 38-40 (Sep./Oct. 1997).

Lund et al., "Long-Term Patentcy of Ductus Arteriosus After Balloon Dilation: an Experimental Study," Laboratory Investigation, 69(4):772-774 (Apr. 1984).

Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™: A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic arch of patients with systemic embolization: A new finding seen by transesophageal echocardiography," *American Heart Journal* 120(3):658-660 (Sep. 1990).

Waksman et al., "Distal Embolization is Common After Directional Atherectomy . . . ," *American Heart Journal*, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

MEDICAL INSTRUMENT WITH CONTROLLED TORQUE TRANSMISSION

FIELD OF THE INVENTION

The invention relates to medical instruments such as guidewires, and more particularly to a medical instrument such as a guidewire that is designed to have controlled torque transmission along its length.

BACKGROUND OF THE INVENTION

Guidewires are used in most catheter-based procedures. The distal end of a guidewire typically has an angled tip, which can be oriented to help steer the guidewire through curves and junctions of the vasculature or vessels of a patient. The orientation of the angled tip is achieved by torquing the guidewire so that it rotates about its axis.

Correct positioning of a catheter is dependent on the ability of the guidewire to track and be rotated to gain access to the target area. Guidewires generally will rotate in a 1:1 ratio between the proximal and distal ends in a straightened position, however, when subject to looping or bending as may occur in a tortuous anatomy, guidewires exhibit the tendency to whip (sudden release of torsional energy). This whipping makes precise access to target sites, such as selecting one vessel of a bifurcation, difficult.

Often, because of the variability of procedures and anatomy, the location of the hoop stress created by looping or bending of the guidewire cannot be predicted. Guidewires that are produced by maintaining a rigid proximal end and sequentially creating a more flexible distal portion are subject to whipping when looping or bending is applied away from the end of the distal portion.

One prior art device and method for torque transmission in a guidewire is shown in U.S. Pat. No. RE 36,628, to Sagae et al. The '628 patent teaches a catheter guidewire wherein the base material constituting the wire is made of an elastic alloy wire and is subjected to a heat treatment such that its flexibility is sequentially increased from its proximal to distal end portions. A thermoplastic resin and/or a coil spring may be applied to at least the distal end portion of the wire base material. A method of manufacturing the catheter guidewire is also taught. The method is characterized in that the leading end side of the base material is divided into a plurality of areas and subjected to a heat treatment by changing the heat treatment temperature and the time conditions in units of the areas so that the flexibility of the base material is sequentially increased from the proximal to distal end portions of the leading end side. As noted above, one of the drawbacks of guidewires such as that taught in the '628 patent is that guidewires that are produced by maintaining a rigid proximal end and sequentially creating a more flexible distal portion are subject to whipping when looping or bending is applied away from the end of the distal portion.

Another prior art device and method for torque transmission is taught in U.S. Pat. No. 5,951,494, which is hereby incorporated by reference. FIGS. 1-3 herein have been reproduced from the '494 patent. Referring to FIG. 1, a guidewire 2 includes a relatively stiff proximal portion 14, a transition portion 16 with varying, intermediate stiffness, and a highly flexible distal portion 18. The guidewire is formed entirely of common medical polymer materials and exhibits high torque fidelity because it has been twisted and tensioned in manufacture to helically orient the polymer. This is illustrated by a segment 8 of the wire that, prior to processing, was parallel to the device axis but after twisting and tensioning, follows a characteristic helical path.

Referring to FIG. 2, in the course of an angioplasty operation to open an occluded coronary artery, the guidewire 2 is typically delivered through an access catheter 20 into the femoral artery 22. The physician pushes and torques the proximal end of the guidewire to thread it through the body into the coronary arteries 24.

Referring to FIGS. 3A and 3B, the distal portion 18 of the guidewire is positioned such that it can cross a restricted region 28 of the artery. The physician pushes (arrow 30) and torques (arrow 32) the proximal portion of the guidewire remaining outside the body. The degree of rotation caused by torquing the proximal end is transmitted to produce a degree of rotation at the distal end.

As noted above, guidewires that are produced by maintaining a rigid proximal end and sequentially creating a more flexible distal portion are subject to whipping when looping or bending is applied away from the end of the distal portion. In addition, guidewires that are formed from certain elastic alloys are relatively expensive to produce. The present invention is directed to a device and method for overcoming the foregoing and other disadvantages. More specifically, the present invention is directed to a medical instrument such as a guidewire that is designed to have controlled torque transmission along its length.

SUMMARY OF THE INVENTION

In accordance with the present invention, a medical instrument such as a guidewire is provided that can be rotated without whipping. In addition to guidewires, other applications include devices such as catheters and driveshafts. In one embodiment, the medical instrument tapers at the distal portion to promote access to anatomy that reduces in inner diameter.

In accordance with another aspect of the invention, specially treated areas are placed in selected and equal areas along the entire length of the elongated shaft of the medical instrument, and are separated from one another by untreated areas. This process ensures that any torque is transmitted distally, in a smooth manner, regardless of the guidewire position, thus resulting in a substantial reduction in whipping. In one embodiment, a stainless steel guidewire is utilized, and is subjected to annealing heat treatment in selected areas. This annealing process will create a mandrel that has repeated temper properties along its length. Torque applied at one end of this mandrel is transmitted to the opposite end in an even and controlled manner, even when the mandrel is formed into a loop.

In accordance with another aspect of the invention, the treated sections are subjected to an annealing process, while the untreated sections are normally tempered. The untreated sections may be longer than the treated sections. In one embodiment, the treated sections are all approximately the same length.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Low carbon alloy steel, such as stainless steel, has strength and hardness imparted through drawing or extrusion. This hardness is an ideal quality for guidewires as they can be torqued effectively over a long length. A guidewire made from this material is very cost effective as compared to a wire made from elastic alloys such as nitinol. An important factor is the ability of the wire to track and thus create a mechanical pathway through a portion of the human anatomy in order to allow a physician to direct other devices such as catheters to a precise location.

The ability to track is related to a combination of both pushing and rotating the guidewire. Often placed in a tortuous path, a guidewire cannot effectively transmit torque from the proximal to the distal end in a 1:1 ratio. As the proximal end is rotated, the torsion is stored as energy in the end of the guidewire proximal to the tortuous path. When the threshold is reached where the stored energy overcomes the resistance of the tortuous path, whipping of the distal tip of the guidewire will occur. As a result, accurate placement of the guidewire is difficult.

Figure 1:
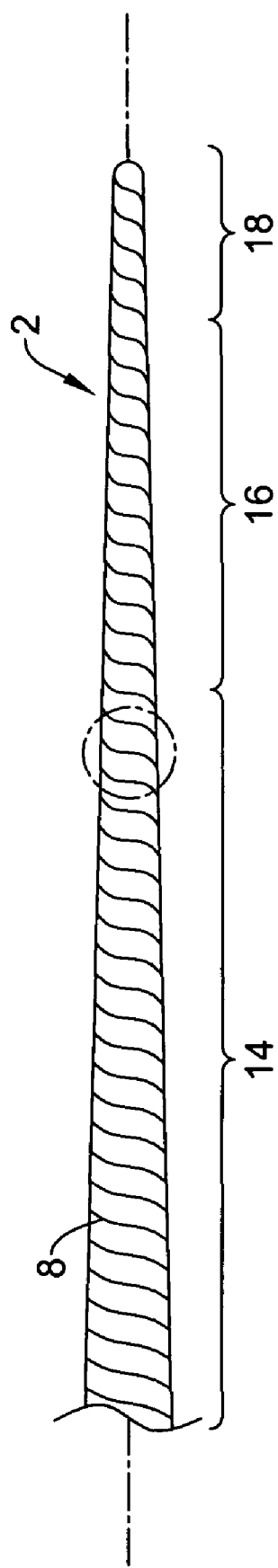
FIG. 1 is a side view of a prior art polymer medical guidewire.
Figure 2:
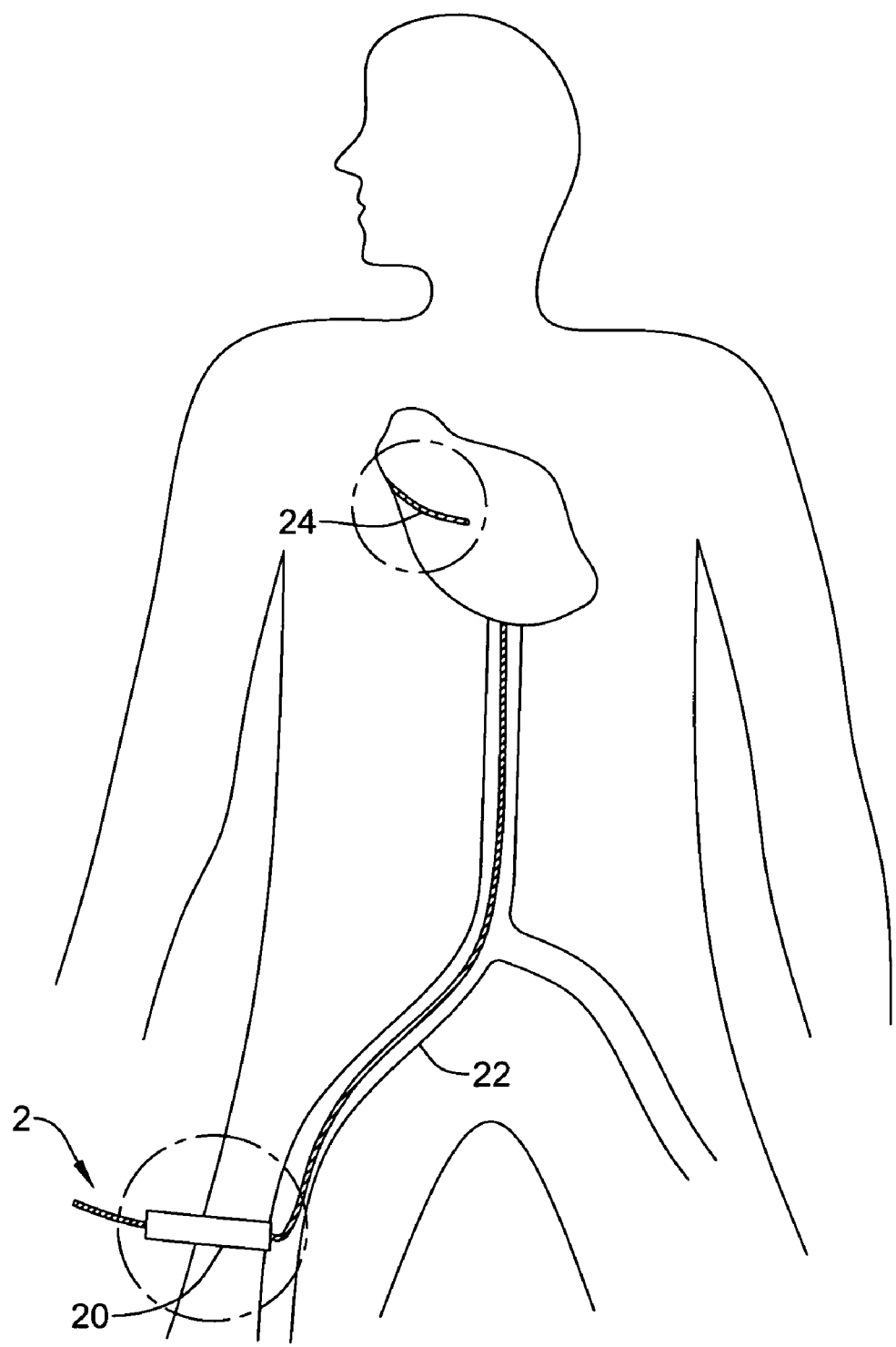
FIG. 2 is a schematic of the prior art guidewire of FIG. 1, as being delivered into a patient.
Figure 3A:
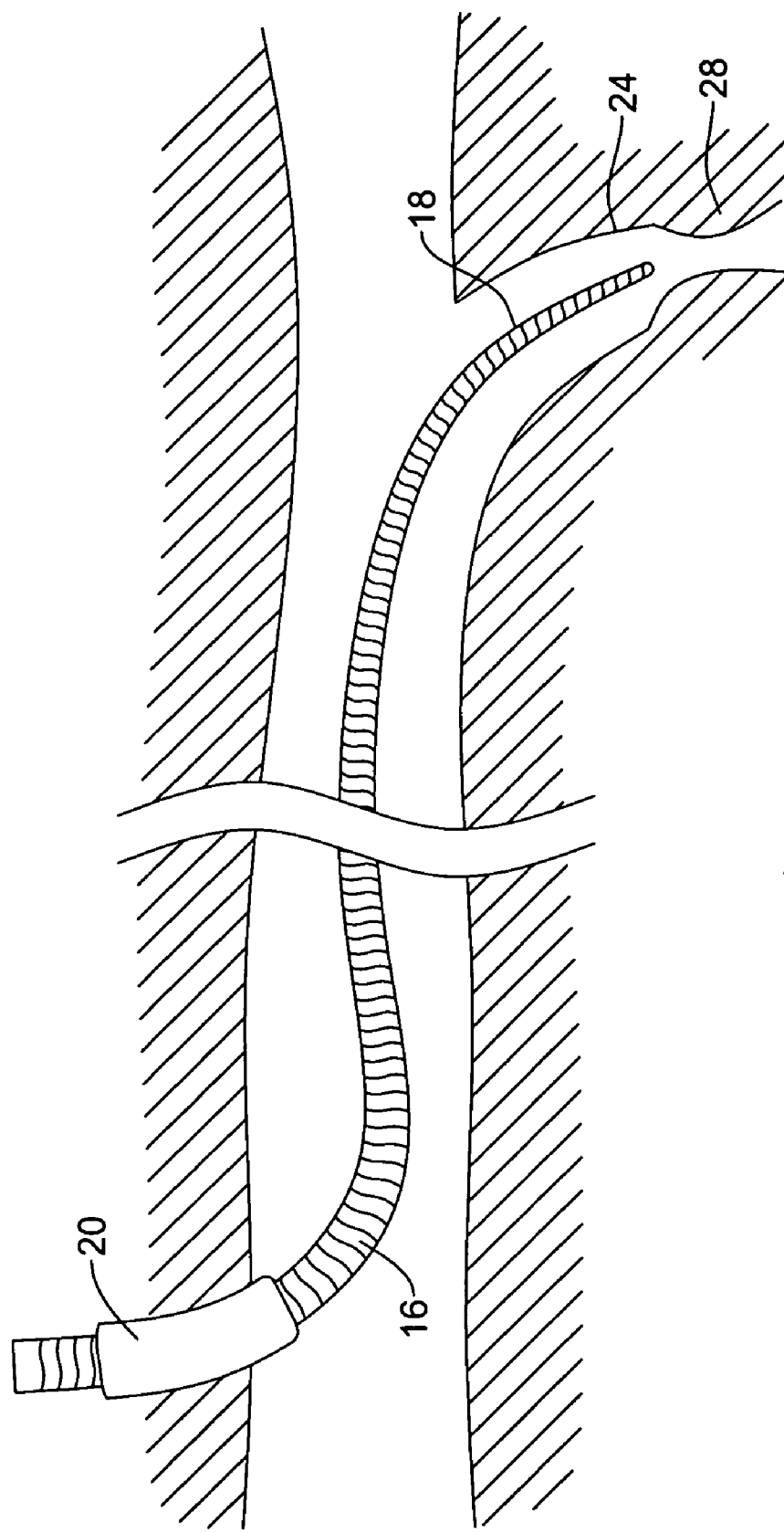
FIGS. 3A and 3B are expanded views of the prior art guidewire of FIG. 2 illustrating torquing of the proximal end and rotation of the distal end.
Figure 3B:
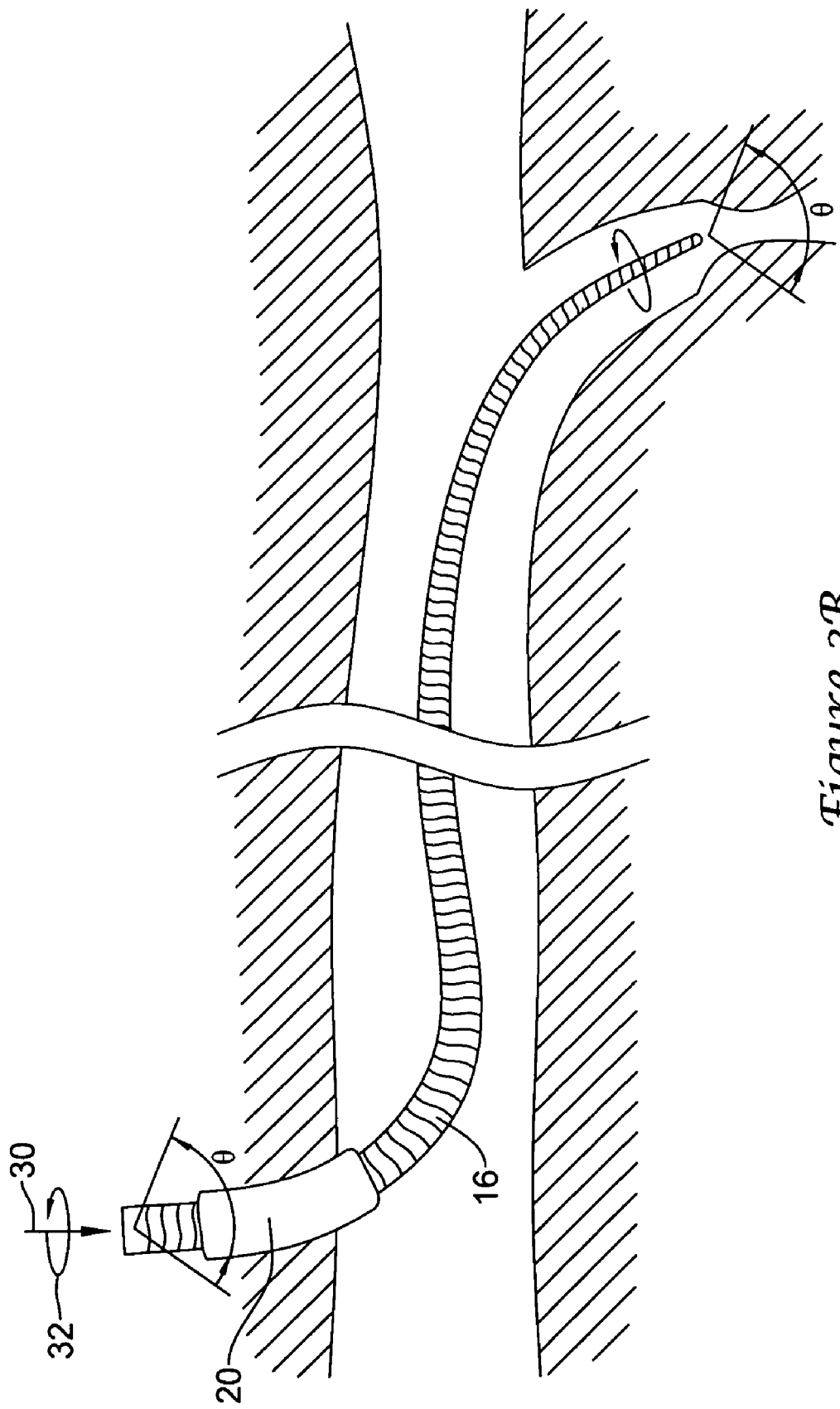
Figure 4:
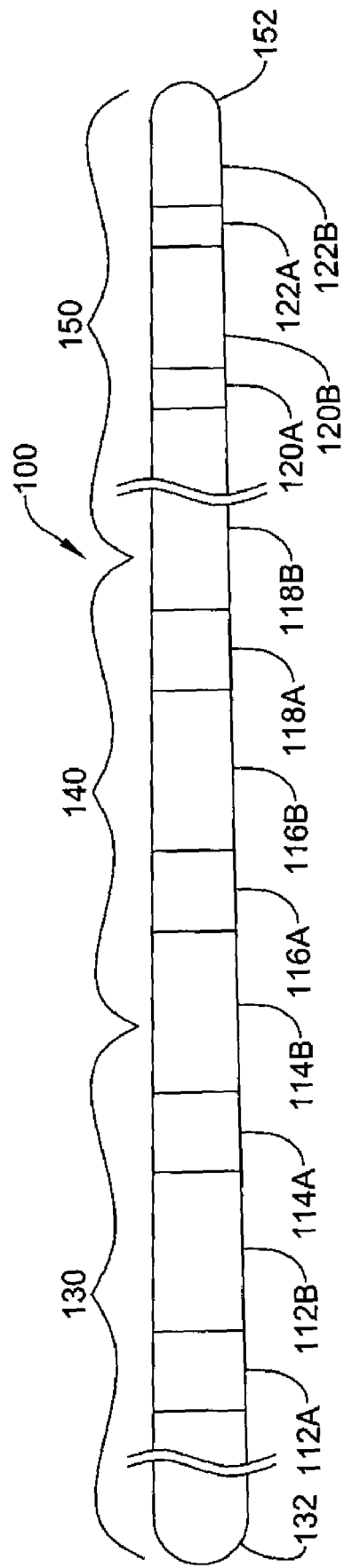
FIG. 4 is a side view of a guidewire that has been subjected to heat treatments in selected areas in accordance with the present invention.

FIG. 4 is a side view of a guidewire 100 that is formed in accordance with the present invention. The guidewire 100 has a proximal end 132, a distal end 152, a proximal section 130 adjacent the proximal end, a distal section 150 adjacent the distal end, and a middle section 150 therebetween. The guidewire 100 has been subjected to selective area annealing. More specifically, localized sections 112a, 114a, 116a, 118a, 120a, and 122a have been subjected to selected area annealing. The sections 112b, 114b, 116b, 118b, 120b, and 122b are untreated (normally tempered) sections.

As noted above, the use of stainless steel as the material is a cost-effective choice for the guidewire 100. In one embodiment, the guidewire 100 comprises an elongated stainless steel element with a length of 220 cm and an outer diameter of 0.018 inches. The stainless steel guidewire 100 is provided with a tapered distal tip. The taper, as in most guidewires, increases the flexibility at the distal end. To improve the ability to push the guidewire 100, the middle and proximal sections are greater in diameter than the distal end. As described above, the middle section may be severely turned as it passes through the aortic arch into the carotid arteries. A curve in the guidewire 100 would be an area where effective torque transmission could be hampered, and which could cause the distal tip to whip upon attempted rotation of the guidewire 100. In this instance, a more ductile middle section that is formed in accordance with the present invention will aid in torque transmission without whipping.

As an example embodiment, in an experiment a guidewire 100 was formed by creating a repeating pattern of 1 cm heat treated (annealed) sections (e.g., 112a, 114a, 116a, 118a, 120a, 122a) followed by 2 cm untreated (normally tempered) sections (e.g., 112b, 114b, 116b, 118b, 120b, 122b). These sections were produced working 20 cm from the proximal end of a 150 cm long, 0.16" diameter stainless steel shaft guidewire 100. In the experiment, to form the guidewire 100 a hydrogen gas generator was fitted with a torch tip that produced a flame 0.030" in diameter and approximately 0.200" long. The annealing temperature for stainless steel is approximately 1200 degrees Fahrenheit. In the experiment, the stainless steel was heated with the hydrogen gas torch until it just changed from a dark red color to a bright red color. In order to create very localized sections, a short annealing time was applied to the 1 cm sections (e.g., 112a, 114a, 116a, 118a). The short annealing time comprised raising each of the sections from room temperature to above 1,280 degrees Fahrenheit over approximately 10 seconds. Heat sinks were used to protect the untreated sections (e.g., 112b, 114b, 116b, 118b). Time as well as heat is important for proper annealing so the heat was allowed to rise above the 1280 degree Fahrenheit mark briefly to compensate for time. The process was followed by a quick quench. Once the guidewire 100 was formed according to this process, it was tested in a looped environment and there was a substantial reduction in whipping for the guidewire 100 as compared with an untreated guidewire of the same material. In other words, upon rotation at the proximal end, a substantial reduction in whipping at the distal end was apparent for the guidewire 100 as compared to an untreated guidewire of the same material.

In actual production, in one embodiment a guidewire 100 may be produced by utilizing RF generation and induction coil heating to achieve selective annealing. Induction heating at precise local areas and for a specific time restores ductility to the heat-treated areas while the hardness of the untreated areas is not compromised. An automated system may be used to control atmosphere, movement, temperature, duration and post process actions such as quenching.

While the preferred embodiment of the invention has been illustrated and described, it will be appreciated that various changes can be made therein without departing from the spirit and scope of the invention. For example, the guidewire may be further coated with materials such as silicone or hydrophilic coatings. In addition, a coiled platinum spring may be provided at the distal end to aid in the flexibility. The guidewire may comprise either a tapered wire from the proximal end to the distal tip, or a straight wire from the proximal end to the distal tip, or any combination thereof. Furthermore, a stainless steel wire base tensile strength can be varied to fit applications where more or less flexibility is required. In addition, a guidewire torque device may be provided to assist with the rotation of the guidewire. Many types of guidewires may benefit from the disclosed method of production, such as neuro/coronary/peripheral vascular guidewires. Other applications include devices such as catheters and driveshafts, as well as other instruments that use shafts which require rotation, such as retrieval baskets and snares. The selective annealing procedure may also aid in the flexibility of devices such as stents, where variable stiffness could aid placement in tortuous anatomy. Various types of metals and materials may be utilized, being either round or non-round, that can be subjected to annealing or tempering.

The embodiments of the invention in which an exclusive property or privilege is claimed are defined as follows:

1. A guidewire comprising:
   an elongated structural body having a proximal end and a distal end, a proximal section adjacent to and including the proximal end, a distal section adjacent to and including the distal end, a middle section therebetween, and a length;
   the body having a plurality of repeated tempered properties within each of the proximal, middle and distal sections;

the repeated tempered properties creating discrete longitudinal sections of the length having annealed properties interspersed with discrete longitudinal sections of the length having normally tempered properties.

2. The guidewire of claim 1, wherein the annealed properties are contained in sections of the structural body that are separated by sections having the normally tempered properties.

3. The guidewire of claim 1, wherein the structural body is tapered along at least part of its length.

4. The guidewire of claim 1, wherein the sections of the structural body that have the normally tempered properties are at least as long as the sections of the body that have the annealed properties.

5. A guidewire comprising:
an elongate member having a proximal section disposed adjacent to and including a proximal end of the guidewire, a distal tip section disposed adjacent to and including a distal end of the guidewire, and a middle section disposed between the proximal section and the distal tip section;
wherein each of the proximal, middle, and distal tip sections further comprises a first plurality of discontinuous longitudinal sections and a second plurality of discontinuous longitudinal sections, wherein the said first and second plurality of discontinuous longitudinal sections alternate along the length of the elongate member within the respective proximal, middle, and distal tip sections;
wherein the first plurality of discontinuous longitudinal sections have been subjected to a tempering process;
the second plurality of discontinuous longitudinal sections not having been subjected to the tempering process; and
wherein the first plurality of discontinuous longitudinal sections and the second plurality of discontinuous longitudinal sections have different torque transmission characteristics.

6. The guidewire of claim 5, wherein the heat treatment process is an annealing process.

7. The guidewire of claim 5, wherein the second plurality of sections are normally tempered.

8. The guidewire of claim 5, wherein each of the sections in the first plurality of sections are approximately the same length.

9. The guidewire of claim 8, wherein each of the sections in the second plurality of sections is approximately twice as long as the sections in the first plurality of sections.

10. The guidewire of claim 5, wherein each of the sections in the second plurality of sections are approximately the same length.

11. The guidewire of claim 5, wherein the guidewire comprises stainless steel.

12. The guidewire of claim 5, wherein the guidewire is tapered along at least part of its length.

13. The guidewire of claim 5, wherein the elongate member is metallic.

* * * * *